United States Patent
Murdeshwar

(10) Patent No.: US 11,547,471 B2
(45) Date of Patent: Jan. 10, 2023

(54) DEVICE WITH LOOP ELECTRODES FOR TREATMENT OF MENORRHAGIA

(71) Applicant: GYRUS ACMI, INC., Southborough, MA (US)

(72) Inventor: Nikhil M. Murdeshwar, Maple Grove, MN (US)

(73) Assignee: Gyrus ACMI, Inc., Westborough, MA (US)

( * ) Notice: Subject to any disclaimer, the term of this patent is extended or adjusted under 35 U.S.C. 154(b) by 371 days.

(21) Appl. No.: 16/365,938

(22) Filed: Mar. 27, 2019

(65) Prior Publication Data
US 2020/0305968 A1    Oct. 1, 2020

(51) Int. Cl.
A61B 18/14    (2006.01)
A61B 18/00    (2006.01)
A61M 25/01    (2006.01)

(52) U.S. Cl.
CPC .. *A61B 18/1485* (2013.01); *A61B 2018/0091* (2013.01); *A61B 2018/00214* (2013.01); *A61B 2018/00559* (2013.01); *A61B 2018/00577* (2013.01); *A61B 2018/1407* (2013.01); *A61B 2018/1467* (2013.01); *A61B 2018/1475* (2013.01); *A61M 2025/0163* (2013.01)

(58) Field of Classification Search
CPC ...... A61B 18/1485; A61B 2018/00214; A61B 2018/00559; A61B 2018/00577; A61B 2018/0091; A61B 2018/1407; A61B 2018/1467; A61B 2018/1475; A61B 2018/126; A61B 18/12; A61B 18/14
See application file for complete search history.

(56) References Cited

U.S. PATENT DOCUMENTS

| | | | |
|---|---|---|---|
| 4,196,734 A | 4/1980 | Harris | |
| 4,493,320 A | 1/1985 | Treat | |
| 4,660,571 A * | 4/1987 | Hess | A61B 5/6858 607/116 |
| 4,763,671 A | 8/1988 | Goffinet | |
| 4,905,691 A | 3/1990 | Rydell | |
| 5,472,442 A | 12/1995 | Klicek | |
| 5,536,267 A | 7/1996 | Edwards et al. | |
| 5,807,392 A | 9/1998 | Eggers | |
| 5,928,229 A | 7/1999 | Gough et al. | |

(Continued)

FOREIGN PATENT DOCUMENTS

| | | |
|---|---|---|
| CN | 111743617 A | 10/2020 |
| EP | 3456278 A2 | 3/2019 |

(Continued)

OTHER PUBLICATIONS

"European Application Serial No. 20166383.8, Extended European Search Report dated Jul. 24, 2020", 8 pgs.

(Continued)

*Primary Examiner* — Linda C Dvorak
*Assistant Examiner* — Lindsay Regan Lancaster
(74) *Attorney, Agent, or Firm* — Schwegman Lundberg & Woessner, P.A.

(57) ABSTRACT

A medical device that has a first array of loop electrodes and a second array of loop electrodes. The first array of loop electrodes and the second array of loop electrodes are configured to expand within a uterus and deliver a therapy current to tissue defining the uterus.

22 Claims, 5 Drawing Sheets

(56) References Cited

U.S. PATENT DOCUMENTS

| | | | |
|---|---|---|---|
| 5,951,546 A | 9/1999 | Lorentzen | |
| 5,980,517 A | 11/1999 | Gough | |
| 5,980,519 A * | 11/1999 | Hahnen | A61B 18/14 600/374 |
| 6,090,105 A | 7/2000 | Zepeda et al. | |
| 6,110,169 A | 8/2000 | Mueller et al. | |
| 6,113,596 A | 9/2000 | Hooven et al. | |
| 6,210,409 B1 | 4/2001 | Ellman et al. | |
| 6,221,071 B1 | 4/2001 | Sherry et al. | |
| 6,231,571 B1 | 5/2001 | Ellman et al. | |
| 6,235,027 B1 | 5/2001 | Herzon | |
| 6,280,441 B1 | 8/2001 | Ryan | |
| 6,352,533 B1 | 3/2002 | Ellman et al. | |
| 6,379,353 B1 | 4/2002 | Nichols | |
| 6,533,778 B2 | 3/2003 | Herzon | |
| 6,572,614 B1 | 6/2003 | Ellman et al. | |
| 6,575,967 B1 | 6/2003 | Leveen et al. | |
| 6,610,056 B2 | 8/2003 | Durgin et al. | |
| 6,840,935 B2 | 1/2005 | Lee | |
| 6,932,814 B2 | 8/2005 | Wood | |
| 7,211,079 B2 | 5/2007 | Treat | |
| 7,276,068 B2 | 10/2007 | Johnson et al. | |
| 7,326,202 B2 | 2/2008 | McGaffigan | |
| 7,416,549 B2 * | 8/2008 | Young | A61B 18/1482 606/41 |
| 7,458,971 B2 | 12/2008 | Zerfas et al. | |
| 7,517,346 B2 | 4/2009 | Sloan et al. | |
| 7,563,273 B2 * | 7/2009 | Goldfarb | A61B 17/12 606/139 |
| 7,670,337 B2 * | 3/2010 | Young | A61B 18/148 606/41 |
| 7,699,805 B2 | 4/2010 | Mulier et al. | |
| 7,794,458 B2 | 9/2010 | McIntyre et al. | |
| 7,862,560 B2 | 1/2011 | Marion | |
| 7,918,795 B2 | 4/2011 | Grossman | |
| 7,922,713 B2 | 4/2011 | Geisei | |
| 8,211,104 B2 | 7/2012 | McCullagh et al. | |
| 8,382,748 B2 | 2/2013 | Geisel | |
| 9,089,337 B2 | 7/2015 | Batchelor et al. | |
| 9,198,719 B2 | 12/2015 | Murdeshwar et al. | |
| 9,439,716 B2 | 9/2016 | Batchelor et al. | |
| 9,839,472 B2 | 12/2017 | Rioux et al. | |
| 2002/0022870 A1 | 2/2002 | Truckai et al. | |
| 2004/0158239 A1 * | 8/2004 | Behl | A61B 18/1477 606/41 |
| 2006/0111702 A1 | 5/2006 | Oral et al. | |
| 2008/0319436 A1 | 12/2008 | Daniel et al. | |
| 2009/0254082 A1 | 10/2009 | Kornerup et al. | |
| 2010/0106152 A1 * | 4/2010 | Truckai | A61B 18/1485 606/33 |
| 2010/0137857 A1 | 6/2010 | Shroff et al. | |
| 2010/0217250 A1 * | 8/2010 | Sampson | A61B 18/1492 606/29 |
| 2010/0268211 A1 | 10/2010 | Manwaring et al. | |
| 2011/0230874 A1 | 9/2011 | Epstein et al. | |
| 2013/0172877 A1 | 7/2013 | Subramaniam et al. | |
| 2018/0055563 A1 * | 3/2018 | Shetake | A61B 5/4325 |

FOREIGN PATENT DOCUMENTS

| | | | | |
|---|---|---|---|---|
| WO | WO-2007001981 A2 * | 1/2007 | | A61B 18/1492 |
| WO | WO-2010053700 A1 | 5/2010 | | |
| WO | WO-2017173089 A1 * | 10/2017 | | A61B 18/1492 |

OTHER PUBLICATIONS

"European Application Serial No. 20166383.8, Response filed Mar. 26, 2021 to Extended European Search Report dated Jul. 24, 2020", 10 pgs.

* cited by examiner

DEVICE WITH LOOP ELECTRODES FOR TREATMENT OF MENORRHAGIA

FIELD

These teachings relate to a device for treating the anatomy, and more particularly to a device with loop electrodes for treatment of menorrhagia.

BACKGROUND

Menorrhagia is a medical condition that includes abnormally heavy and prolonged menstrual bleeding and pain. For decades, hormone pills and/or hysterectomy were used to treat menorrhagia.

Recently, medical devices have been introduced to treat menorrhagia by way of endometrium ablation, where the endometrium is exposed to various treatment modalities such as RF energy, cryogenics, thermal energy, microwave energy, and/or steam.

It may be desirable to improve the current state of the art by having a medical device that is configured to globally treat the uterus and reduce or eliminate risk of tissue perforation.

SUMMARY

These teachings provide a medical device. The medical device is configured to globally treat a uterus while reducing or eliminating risk of tissue perforation.

The medical device has a first array of loop electrodes and a second array of loop electrodes. The first array of loop electrodes and the second array of loop electrodes are configured to extend and/or expand from the medical device and deliver a therapy current to tissue defining the uterus. The first array of loop electrodes and the second array of loop electrodes are configured to retract or collapse into the medical device.

The medical device according to these teachings includes an array of loop electrodes comprising two or more loops electrodes that are arranged in a single plane. The array of loop electrodes is configured to extend and/or expand from the medical device within a uterus and deliver a therapy current to the uterus.

The medical device according to these teachings includes an array of loop electrodes. The array comprises three or more loops electrodes that are circumferentially arranged about an axis of the medical device and. The array of loop electrodes is configured to extend and/or expand within a uterus and deliver a therapy current to tissue defining the uterus.

A medical device comprising a distal array of loop electrodes comprising a first loop electrode and a second loop electrode; and a proximal array of loop electrodes comprising a first loop electrode and a second loop electrode. A first conductor wire forms the first loop electrode of the distal array of loop electrodes and the first loop electrode of the proximal array of loop electrodes. A second conductor wire forms the second loop electrode of the distal array of loop electrodes and the second loop electrode of the proximal array of loop electrodes. The distal array of loop electrodes and the proximal array of loop electrodes are configured to expand within a uterus and deliver a therapy current to tissue defining the uterus.

The medical device according to these teachings is configured to create, apply, and/or produce a global therapeutic effect on tissue inside of a body cavity like a uterus. The global therapeutic effect is achieved with the medical device according to these teachings without requiring surface to surface contact of the medical device with the body cavity. Instead, the global therapeutic effect is achieved with a point or electrode to surface contact with the body cavity. A therapy current may be passed between two or more loop electrodes according to these teachings that are in contact with tissue of the body cavity to paint a set of therapy regions that can together produce the global therapeutic effect on or within the body cavity.

DETAILED DESCRIPTION

Figure 1:
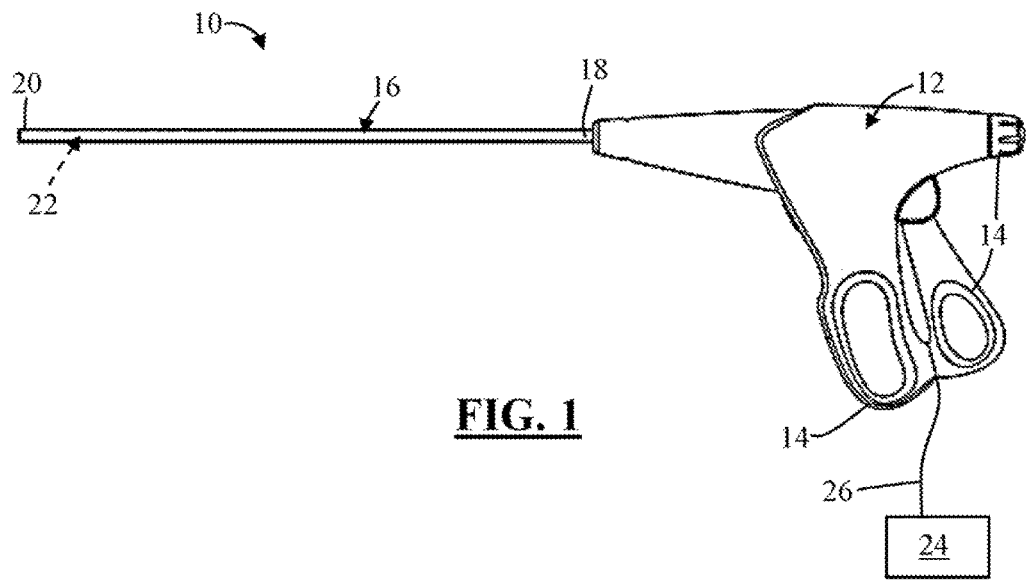
FIG. 1 is a side view of a medical device.

These teachings relate to a medical device. The medical device may be used to treat or effect an anatomical feature. The anatomical feature may be any anatomical feature, such as a body cavity or a body lumen. The body cavity may be a uterus. The medical device may be configured to treat menorrhagia. The medical device may be configured to effect or destroy the endometrium by ablation. The medical device may be used to treat or effect an anatomical feature passing a therapy current between or amongst two or more loop electrodes causing a feature of the anatomy in contact with the two or more loop electrodes to heat up to or beyond an ablative temperature.

The medical device according to these teachings is configured to provide global treatment of the body cavity or uterus. That is, by supplying or passing a therapy current between two or more loop electrodes that are in contact with the anatomy, a global or full surface treatment of the tissue of the body cavity can be achieved substantially the same time, as opposed to locally or discretely treating only certain areas of tissue as may be the case with other medical devices that utilize direct or targeted treatment methods.

While the medical device disclosed herein may be used to treat menorrhagia, it is understood that the medical device can be used in other applications as well. For example, the device and system can be used to treat or ablate tissue in the bladder, vagina, esophagus, trachea, urethra, ureter, prostate gland, kidney, intestinal growths or abnormal tissues of the intestine, cancerous tissue, etc.

The medical device comprises a hand piece. The hand piece may function to be held by a user or robot.

The medical device and/or the hand piece may comprise one or more user controls. Movement or manipulation of the one or more user controls may function to move or actuate the effector; supply, increase, and/or decrease an intensity of the therapy current to the one or more loop electrodes; or a combination thereof.

Movement or manipulation of the one or more user controls may function to move the effector between or into the collapsed state and the expanded state. Movement or manipulation of the one or more user controls may function to move the carrier into the introducer in a proximal direction and also move the carrier out of the introducer in a distal direction.

Movement or manipulation of the one or more user controls may function to rotate the effector about the longitudinal axis of the carrier and/or introducer.

Movement or manipulation of the one or more user controls may function to cause the first or distal array of loop electrodes to move or expand out of or away from the distal end of the carrier. Movement or manipulation of the one or more user controls may function to cause the first or distal array of loop electrodes to move into or retract into the distal end of the carrier.

Movement or manipulation of the one or more user controls may function to cause the second or proximal array of loop electrodes to move or expand out of or away from the outer surface of the carrier. Movement or manipulation of the one or more user controls may function to cause the second or proximal array of loop electrodes to move into or retract into one or more openings defined in the carrier.

The one or more user controls may be one or more switches, levers, buttons, triggers, knobs, rotation wheels, or a combination thereof. The one or more user controls may also be a foot pedal in communication with the medical device.

The medical device comprises an introducer. The introducer may function to permit a portion of the medical device to be inserted into a patient, anatomy, or body cavity, while a portion of the device remains outside of the patient, anatomy, or body cavity.

The introducer may be a tubular member. The introducer may be a braided or coiled tube. The introducer may be a tube that is generally smooth on the inside and outside surfaces. The introducer may be an elongated member that extends along a longitudinal axis. The proximal end or proximal portion of the introducer may be connected to the hand piece. The introducer may have a relatively small diameter, on the order of about 10 mm or less, 9 mm or less, 8 mm or less, 7 mm or less, or even 6 mm or less. Preferably, the diameter of the introducer may be less than 5 mm. Such relatively small sized introducer may be advantageous in minimizing patient trauma during insertion and/or removal of the introducer into and from a body cavity.

The introducer may be substantially straight and/or may include sections that are substantially straight; may include one or more angles, bends or arcs and/or may include sections that have one or more angles, bends or arcs; or a combination thereof. The introducer may be substantially rigid, substantially flexible, substantially resilient, substantially kink-resistant, or a combination thereof. The introducer may be configured in such a way to allow angular movements and/or can be advanced along a tortuous path within a body lumen and/or body cavity.

The introducer may comprise an inner portion, channel, or lumen. The inner portion, channel, or lumen may provide an area or passageway for one or more conductors to extend between the power source and the effector, the one or more loop electrodes, or both. Alternatively, the one or more conductors may extend along or across an outside surface of the introducer.

The inner portion, channel, or lumen of the introducer may provide an area or passageway for the effector. The effector may be at least partially located inside of the introducer when the effector is in the expanded, forward, or distal position or state, in the retracted, rearward, or proximal position or state; or both.

The medical device may comprise one or more effectors. An effector may be any portion of the medical device that is configured to contact and/or effect or treat an anatomical feature. The effector may function to come into contact and/or apply direct pressure onto one or more portions of the body cavity or anatomy to medically effect the body cavity or anatomy.

The effector may function to provide and/or pass a therapy current between two or more loop electrodes that are in contact with the anatomy to ablate the tissue or anatomy in contact with the loop electrodes. The effector may function to globally ablate the body cavity by passing one or more therapy currents between two or more loop electrodes that are in contact with tissue in various areas of the body cavity without requiring a user to rotate, sweep, or otherwise reposition the effector inside of the body cavity. Advantageously, by globally ablating the body cavity by passing the therapy current between or amongst the various loop electrodes, time required to ablate an entire body cavity is reduced. Moreover, by not having to rotate, sweep, or otherwise reposition the effector inside of the body cavity to ablate the entire body cavity, risk of tissue perforation and/or irritation may be reduced or eliminated.

The effector may include one or more carriers, one or more loop electrodes, one or more electrode arrays, or a combination thereof. The effector may be moveable between an expanded, forward, or distal position, and a retracted rearward, or proximal position. The effector may be moved between the two positions by manipulating, one or more of the user controls.

The expanded, forward, or distal position of the effector may be when at (east one loop electrode is located distal of the distal end of the introducer. The expanded, forward, or distal position of the effector may be when only the first or distal array of loop electrodes is located distal of the distal end of the introducer. The expanded, forward, or distal position of the effector may be when only the second or proximal array of loop electrodes is located distal of the distal end of the introducer. The expanded, forward, or distal position of the effector may be when both of the first or distal array of loop electrodes and the second or proximal loop electrodes are located distal of the distal end of the introducer.

In the expanded position, one or more of the loop electrodes may extend from the carrier. In the expanded position, one or more of the loop electrodes in the first or distal array of loop electrodes may extend or project out of or distally from a distal-most end of the carrier. In the expanded position, one or more of the loop electrodes in the second or proximal array of loop electrodes may extend or project circumferentially around an axis of the carrier. In the expanded position, one or more of the loop electrodes in the first or distal array of loop electrodes may extend or project out of or distally from a distal-most end of the carrier and one or more of the loop electrodes in the second or proximal array of loop electrodes may extend or project circumferentially around an axis of the carrier.

The retracted, rearward, or proximal position of the effector may be when at least one loop electrode is located proximal of the distal end of the introducer. The retracted, rearward, or proximal position of the effector may be when only the second or proximal array of loop electrodes is located proximal of the distal end of the introducer. The retracted, rearward, or proximal position of the effector may be when only the first or distal array of loop electrodes is located proximal of the distal end of the introducer. The retracted, rearward, or proximal position of the effector may be when both the second or proximal array of loop electrodes and the first or distal array of loop electrodes are located proximal of the distal end of the introducer.

In the retracted position, one or more of the loop electrodes may be at least partially located inside of the carrier and/or the introducer. In the retracted position, one or more of the loop electrodes in the first or distal array of loop electrodes may be located inside of the carrier and/or the introducer, or may be located between an outer surface of the carrier and an inner surface of the introducer. In the retracted position, one or more of the loop electrodes in the second or proximal array of loop electrodes may be located inside of the carrier and/or the introducer, or may be located between an outer surface of the carrier and an inner surface of the introducer.

The effector may include one or more carriers. A carrier may function to support the one or more electrode arrays and/or loop electrodes. A carrier may function to be moved relative to a stationary introducer and/or hand piece. The carrier can be moved by manipulating the one or more user controls. Distal movement of the carrier moves the effector into the expanded, distal, or forward position. Proximal movement of the carrier moves the effector into the retracted, proximal, or rearward position.

The carrier may be a hollow member. The carrier may include a distal most end. The one or more loop electrodes in the first or distal array of loop electrodes may be configured to spring out of or extend out of the distal most end of the carrier when the effector is in the expanded, distal, or forward position or state. The one or more loop electrodes in the first or distal array of loop electrodes may be configured to collapse into or inside of the distal most end of the carrier when the effector is in the retracted, proximal, or rearward position or state.

Alternatively, when the effector is in the retracted, proximal, or rearward position, the loop electrodes of the first or distal array of loop electrodes may be configured to lay or rest against or adjacent an outer surface of the carrier. In such a configuration, when the effector is in the retracted, proximal, or rearward position, the loop electrodes of the first or distal array of loop electrodes may be provided between an outer wall or surface of the effector and the inner wall or surface of the effector.

The carrier may include one or more openings or slots. The one or more openings or slots may be located proximal of the distal-most end of the carrier. The one or more loop electrodes in the second or proximal array of loop electrodes may be configured to spring out of or extend out of one or more openings or slots defined in the carrier when the effector is in the expanded, distal, or forward position. The one or more loop electrodes in the second or proximal array of loop electrodes may be configured to collapse into the openings or slots of the carrier when the effector is in the retracted, proximal, or rearward position.

Alternatively, when the effector is in the retracted, proximal, or rearward position, the loop electrodes of the second or proximal array of loop electrodes may be configured to lay against or adjacent an outer surface of the carrier. In such a configuration, when the effector is in the retracted, proximal, or rearward position, the loop electrodes of the second or proximal array of loop electrodes may be provided between an outer wall or surface of the effector and the inner wall or surface of the effector.

The medical device or effector comprises one or more arrays of loop electrodes. The medical device or effector may comprise one or more arrays of loop electrodes; two or more arrays of loop electrodes; three or more arrays of loop electrodes; etc. Each array of loop electrodes may comprise two or more loop electrodes.

The medical device or effector comprises a first or distal array of loop electrodes. The first or distal array of loop electrodes may be located distal of any other loop electrodes or arrays of loop electrodes. The first or distal array of loop electrodes may extend from a distal-most end of the effector, introducer, medical device, or a combination thereof. In some configurations, the first or distal array of loop electrodes may extend from an outer side or surface of the effector.

The first or distal array of loop electrodes may comprise one or more loop electrodes. The first or distal array of loop electrodes may comprise only two loop electrodes. The first or distal array of loop electrodes may comprise only three loop electrodes. The first or distal array of loop electrodes may comprise four or more loop electrodes.

One or more of the loop electrodes in the first or distal array of loop electrodes may be generally or substantially planar. This means that the loop electrode(s) fits on or within a single plane. Two or more of the loop electrodes in the first or distal array of loop electrodes may be coplanar or may fit on or within a single plane. Two or more of the loop electrodes in the first or distal array of loop electrodes may be coplanar or may fit within the shape or anatomy of the uterus.

Alternatively, in some configurations, the loop electrodes in the first or distal array of loop electrodes may be arranged in two or more planes. Alternatively, in some configurations, the loop electrodes in the first or distal array of loop electrodes may be configured to extend around at least a portion of the outer surface of the carrier and/or axis.

The loop electrodes in the first or distal array of loop electrodes may have a petal shape or a triangular shape, discussed further below.

The loop shape of the electrodes function to provide a spring or compliant member when the loop electrodes are in contact with the anatomy of the body cavity to maintain pressure on the anatomy. The loop electrodes have a blunt or rounded tip to reduce or minimize tissue perforation or irritation.

The medical device or effector comprises a second or proximal array of loop electrodes. The second or proximal array of loop electrodes may be located proximal of any other loop electrodes or arrays of loop electrodes. The second or proximal array of loop electrodes may extend from an outer surface or portion of the effector, introducer, medical device, or a combination thereof.

The second or proximal array of loop electrodes may comprise one or more loop electrodes. The second or proximal of loop electrodes may comprise only two loop electrodes. The second or proximal array of loop electrodes may comprise only three loop electrodes. The second or proximal array of loop electrodes may comprise four or more loop electrodes.

The one or more loop electrodes in the second or proximal of loop electrodes arranged in two or more planes. The loop electrodes in the second or proximal array of loop electrodes may be configured to extend around at least a portion of the outer surface of the carrier and/or axis. The loop electrodes in the second or proximal array of loop electrodes may be equally spaced about the outer surface of the carrier or longitudinal axis. For example, each of the loop electrodes in the second or proximal array of loop electrodes may be arranged or spaced apart about 60 degrees from each other around the introducer. The loop electrodes in the second or proximal array of loop electrodes may extend around the introducer in a single plane. Alternatively, the spacing between the loop electrodes in the second or proximal array of loop electrodes may be random or unequal—meaning a space between two adjacent loop electrodes may be different than a spacing between two other adjacent loop electrodes in the second or proximal array of loop electrodes.

Alternatively, the one or more loop electrodes in the second or proximal of loop electrodes may be generally or substantially planar. This means that the loop electrode(s) fits on or within a single plane. Two or more of the loop electrodes in the second or proximal array of loop electrodes may be coplanar or may fit on or within a single plane. The plane that the two or more loop electrodes in the second or proximal array of loop electrodes may be generally perpendicular to the introducer.

The loop electrodes in the second or proximal array of loop electrodes may have a petal shape or a triangular shape, discussed further below.

The medical device, the effector, the one or more arrays of loop electrodes, or a combination thereof may include one or more loop electrodes.

A loop electrode is may be a member that is formed into a loop or circle. The member may be a wire, a conductor, an electrode, or a combination thereof. The member may be electrically conductive. The member may be non-electrically conductive but may include one or more electrodes or plates that are electrically conductive attached to the member. The member may include electrodes painted on the member.

The loop electrodes may be in electrical communication with the power source.

The loop electrodes may be configured to expand or spring out of the carrier or introducer and into direct contact with and apply a pressure onto an anatomical feature of the body cavity, like tissue, a wall, a fundus, a cornu, fallopian tube, etc. A therapy current may be passed between or amongst one or more of the loop electrodes to medically effect the body cavity in contact with the one or more loop electrodes.

The one or more loop electrodes may be made of a material that may deflect, bend, compress or conform to tissue defining the body cavity when in contact the tissue. This allows the medical device, the effector, and/or the array of loop electrodes to confirm to different body cavities to ensure the loop electrodes are in direct contact with the anatomical feature. The one or more loop electrodes may be made of a wire like shape memory alloy (SMA) that has elastic properties that expand to fit inside of the body cavity.

The loop electrodes in any of the arrays of loop electrodes may have a petal shape or a triangular shape.

A petal shape means a loop electrode that has two opposing legs that extend between a base and a tip. One or both of the legs and/or the tip may be configured to directly contact one or more features of the anatomy or body cavity. One or both of the legs may be generally straight or linear, or one or both of the lees may be curved or bent. One or both of the legs may bend towards or away from an opposing leg. The tip may be rounded or blunt surface or edge to reduce or prevent tissue irritation or perforation. When the tip of the petal shaped loop electrode is in contact with the anatomical feature, the pressure on the tip may cause the tip to move towards the base, which may cause one or both of the legs to move or deflect away from each other. Advantageously, this allows for the loop electrode to deform or deflect to accommodate various sizes of body cavities, while ensuring a sufficient contact is made and maintained with the anatomical feature. Additionally, or alternativity, pressure on the tip may cause the loop electrode to move or at least partially collapse into an opening or slot of the carrier.

A triangular shape means a loop electrode that has two opposing legs that extend between a base and a tip. One or both of the legs and/or the tip may be configured to directly contact one or more features of the anatomy or body cavity. One or both of the legs may be generally straight or linear, or one or both of the legs may be curved or bent. One or both of the legs may bend towards or away from an opposing leg. The tip may be rounded or blunt surface or edge to reduce or prevent tissue irritation or perforation. The base may be wider or longer than the tip. When the tip of the triangular shaped loop electrode is in contact with the anatomical feature, the pressure on the tip may cause the tip to move or deflect, which allows for the loop electrode to deform or deflect to accommodate various sizes of body cavities, while ensuring a sufficient contact is made and maintained with the anatomical feature. Additionally, or alternativity, pressure on the tip may cause the loop electrode to move or at least partially collapse into an opening or slot of the carrier.

The power source may be configured to deliver electrical energy, such as radio frequency (RF) energy to the medical device, the effector, the one or more loop electrodes or a combination thereof. The electrical energy may be a therapy current. The electrical energy or therapy current may be a bipolar therapy signal.

The power source may be part of or contained in the medical device, for example in the hand piece, the effector, the introducer, or a combination thereof. The power source may be a generator or wall outlet that is located a distance away from the medical device and electrically connected to the effector, loop electrodes, or both via one or more wires, conducts, and/or plugs.

FIG. 1 illustrates a medical device 10. The medical device 10 comprises a hand piece 12. The medical device 10 and/or the hand piece 12 comprises one or more user controls 14 for operating, manipulating, and/or using the medical device 10.

The medical device 10 comprises an introducer 16 that has a proximal end 18 connected to the hand piece 12 and an opposing distal end 20. The medical device 10 comprises an effector 22. The effector 22 is illustrated in a collapsed or retracted state inside of the introducer 16. The medical device 10 and/or the effector 22 is in electrical communication with a power source 24 via one or more electrical conductors or wires 26.

Figure 2:
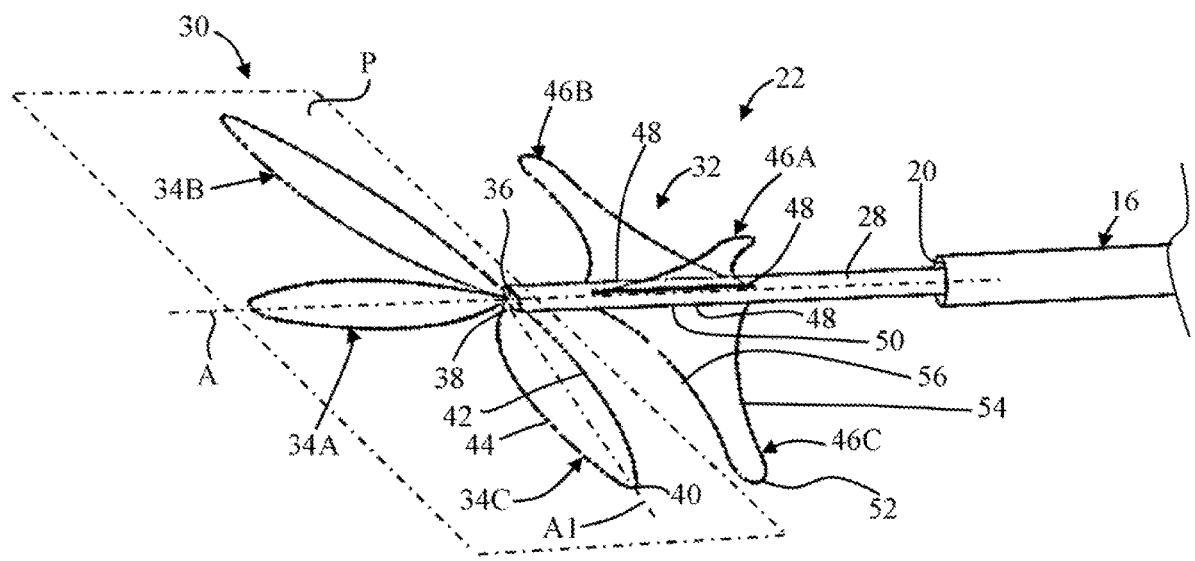
FIG. 2 is a perspective view of a distal portion of the medical device of FIG. 1, with the first and second arrays of loop electrodes in an expanded or extended state.

FIG. 2 illustrates a distal portion of the medical device 10. The effector 22 is shown in an expanded or extended state. The effector 22 comprises a carrier 28, a first array of loop electrodes 30, and a second array of loop electrodes 32. The carrier 28 is configured to be moved in a proximal and distal direction relative to the introducer 16 and the hand piece 12 (FIG. 1). In FIG. 1, the effector 22 is in a collapsed or retracted state, where the carrier 28 is retracted into or collapsed inside of the introducer 16 or moved in a proximal direction towards the hand piece 12, through an opening defined at the distal end 20 of the introducer 16. In FIG. 2, the effector 22 is in an extended or expanded state, where the carrier 28 is moved in a distal direction away from the hand piece 12 and out of the distal end 20 of the introducer 16. The carrier 28 is configured to move between the expanded and collapsed states by manipulating one or more of the user controls 14 (FIG. 1). The carrier 28 extends along a longitudinal axis A, which may be the same longitudinal axis that the introducer 16 extends along.

The first array of loop electrodes 30, which may also be referred to as a distal array of loop electrodes, comprises loop electrodes 34A, 34B, 34C, which are located distal of the second array of loop electrodes 32, or the proximal array of loop electrodes.

When the effector 22 is in the expanded or extended state (FIG. 2), the loop electrodes 34A, 34B, 34C are configured to extend or expand distally out of or from an opening defined in the distal-most end 36 of the medical device 10 or the carrier 28. When the effector 22 is in the collapsed or retracted state (FIG. 1), the loop electrodes 34A, 34B, 34C are at least partially retracted or collapsed or located inside of the carrier 28. More specifically, at least a portion of one or more of the loop electrodes 34A, 34B, 34C are at least partially retracted or collapsed into the opening defined at the distal-most end 36 of the medical device 10 or the carrier 28 when the effector 22 is in the collapsed or retracted state.

Each of the loop electrodes 34A, 34B, 34C in the first array of loop electrodes 30 is individually, electrically connected to the power source 24 (FIG. 1). This means that one or more wires or conductors that form each loop 34A, 34B, 34C is/are electrically connected to the power source 24 (FIG. 1) so that each loop 34A, 34B, 34C has an electrical potential depending on the pole of the power source 24 that the loop 34A, 34B, 34C is connected to, or depending on the potential being transmitted from the power source 24 to the loop 34A, 34B, 34C. For example, the wire or wires used to form loop 34A may be configured to provide a positive potential, the wire or wires used to form loop 34B may be configured to provide a negative potential, and the wire or wires used to form loop 34C may be configured to provide a negative potential, or any combination thereof. The power source 24 may also be configured to switch the electrical potential output from the power source 24 so that, for example, during one therapeutic application, loop 34A may be configured to provide a positive potential, loop 34B may be configured to provide a negative potential, and loop 34C may be configured to provide a negative potential, and during another therapeutic application, loop 34A may be configured to provide a negative potential, loop 34B may be configured to provide a positive potential, and loop 34C may be configured to provide a positive potential.

One or more of the loop electrodes 34A, 34B, 34C in the first array of loop electrodes 30 has a petal shape. Referring to loop electrode 34C, a petal shape means that the loop electrodes 34A, 34B, 34C have a base 38; a tip 40; and a pair of legs 42, 44 between the base 38 and the tip 40. The legs 42, 44 are curved or bow outwardly away from each other 42, 44 between the base 38 and tip 40. The base 38 and the tip 40 may be generally the same size and arranged along a common axis A1. The tip 40 may be rounded or blunt to restrict or prevent tissue irritation or perforation when the tip 40 makes contact with the tissue or walls defining the body cavity. The petal-shaped loop electrodes 34A, 34B, 34C are configured to compress, deform, at least partially conform, and/or apply and maintain substantially equal pressure on the body cavity after the tip 40 makes contact with the tissue or walls defining the body cavity. For example, after contact between the tip 40 and tissue is made, the one or both of the legs 42, 44 may deform or bow further apart from one another or move towards each other, while the tip 40 is moved or compressed towards the base 38. Additionally, or alternatively, while the tip 40 is moved or compressed towards the base 38, the base 38 and/or legs 42, 44 may be at least partially moved or collapsed into the opening at the distal-most end 36 of the medical device 10 or the carrier 28.

Each of the loop electrodes 34A, 34B, 34C are flat or planar and/or located on a plane P. Two or more of the electrodes 34A, 34B, 34C are coplanar or arranged in or disposed on a common plane P.

The second array of loop electrodes 32 comprises loop electrodes 46A, 46B, 46C. In the expanded or extended configuration, the loop electrodes 46A, 46B, 46C are configured to expand or extend from an area of the medical device 10 or carrier 28 that is proximal to the distal-most end 36 of the medical device 10 or carrier 28. The loop electrodes 46A, 46B, 46C are configured to expand or extend from an area of the medical device 10 or carrier 28 that is proximal to the loop electrodes 34A, 34B, 34C in the first array of loop electrodes 30. The loop electrodes 46A, 46B, 46C are configured to expand or extend from one or more openings or slits 48 defined in the carrier 28. When the device 10 is in the retracted or collapsed state (FIG. 1), the loop electrodes 46A, 46B, 46C may be configured to at least partially or completely retract or collapse into the carrier 28 via the one or more openings or slits 48 defined in the carrier 28.

When the effector 22 is in the extended or expanded state, the loop electrodes 46A, 46B, 46C are circumferentially arranged around or about the carrier 28 and/or around the axis A. The loop electrodes 46A, 46B, 46C are generally equally spaced around or about the carrier 28 and/or around the axis A. This means that a distance or gap or spacing between each of the loop electrodes 46A, 46B, 46C around or about the carrier 28 and/or around the axis A is substantially the same. However, in some other configurations, the distance or gap or spacing between each of the loop electrodes 46A, 46B, 46C around or about the carrier 28 and/or around the axis A may be different.

Each of the loop electrodes 46A, 46B, 46C in the second array of loop electrodes 32 is individually, electrically connected to the power source 24 (FIG. 1). This means that one or more wires or conductors that form each loop 46A, 46B, 46C is/are electrically connected to the power source 24 (FIG. 1) so that each loop 46A, 46B, 46C has an electrical potential depending on the pole of the power source 24 that the loop 46A, 46B, 46C is connected to, or depending on the potential being transmitted from the power source 24 to the loop 46A, 46B, 46C. For example, the wire or wires used to form loop 46A may be configured to provide a positive potential, the wire or wires used to form loop 46B may be configured to provide a negative potential, and the wire or wires used to form loop 46C may be configured to provide a negative potential, or any combination thereof. The power source 24 may also be configured to switch the electrical potential output from the power source 24 so that, for example, during one therapeutic application, loop 46A may be configured to provide a positive potential, loop 46B may be configured to provide a negative potential, and loop 46C may be configured to provide a negative potential, and during another therapeutic application, loop 46A may be configured to provide a negative potential, loop 46B may be configured to provide a positive potential, and loop 46C may be configured to provide a positive potential.

One or more of the loop electrodes 46A, 46B, 46C in the second array of loop electrodes 32 has a triangular shape. Referring to loop electrode 46C, a triangular shape means that the loop electrodes 46A, 46B, 46C have a base 50, a tip 52, and legs 54,56 extending between the base 50 and the tip 52. The base 50 is wider than the tip 52. The tip 52 may be rounded or blunt to reduce or eliminate tissue irritation and/or perforation Each of the legs 54, 56 are curved or bent towards each other 54, 56 as the legs 54, 56 extend from the base 50 towards the tip 52. The triangular-shaped loop electrodes 46A, 46B, 46C are configured to compress, deform, at least partially conform, and/or apply and maintain substantially equal pressure on the body cavity after the tip 52 makes contact with the tissue or walls defining the body cavity. For example, after contact between the tip 52 and tissue is made, the one or both of the legs 54, 56 may deform or move further apart from one another or towards each other, while the tip 52 is moved or compressed towards the base 50. Additionally, or alternatively, the base 50 and/or legs 54, 56 may be at least partially moved or collapsed into the openings or slits 48 defined in the carder 28 or medical device 10 after contact between the tip 52 and tissue is made.

Figure 3:
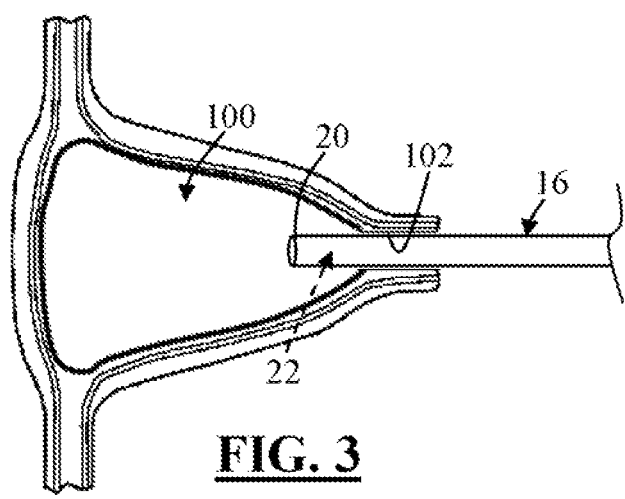
FIG. 3 is a side view of a distal portion of the medical device of FIG. 1 inserted into a body cavity, with the first and second arrays of loop electrodes in a collapsed or retracted state.

FIG. 3 illustrates the distal end 20 of the introducer 16 located within a body cavity 100. The body cavity 100 may be a uterus. The body cavity 100 comprises a cervical canal or opening 102 through which the introducer 16 can be inserted into the body cavity 100. The effector 22 is illustrated in a collapsed or retracted state inside of the introducer 16. The effector 22 may be in the collapsed state during insertion and extraction of the medical device 10 and/or introducer 16 into and from the body cavity 100. In the collapsed or retracted state, the first and second arrays of loop electrodes 30, 32 are at least partially collapsed or retracted inside of the carrier 28 and/or introducer 16. For example, the first array of loop electrodes 30 may be retracted or collapsed into the opening at the distal-most end of the carrier 28, while the second array of loop electrodes 32 may be collapsed or retracted into the openings or slits 48 defined in the carrier 28.

Figure 4:
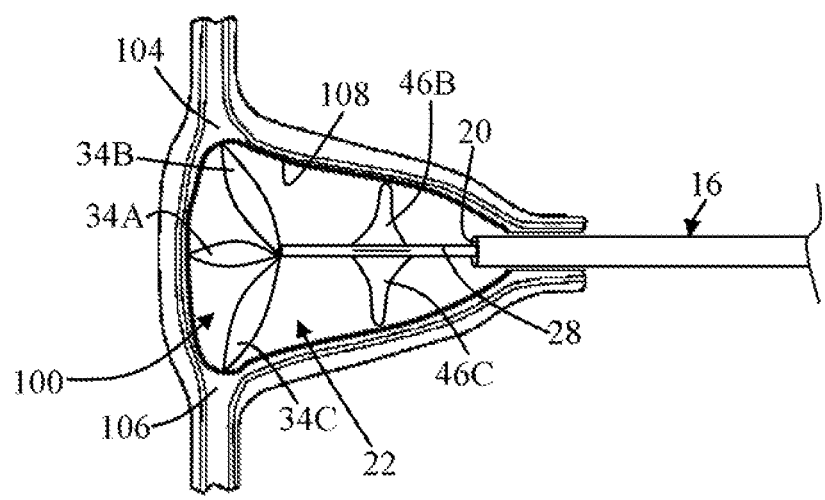
FIG. 4 is a side view of a distal portion of the medical device of FIG. 1 inserted into a body cavity, with the first and second arrays of loop electrodes in an expanded state.

FIG. 4 illustrates the effector 22 in the expanded state inside of the body cavity 100. In the expanded state, one of the loop electrodes 34B of the first array a loop electrodes 30 is configured to contact or enter into a first cornu 104 of the body cavity 100, another one of the loop electrodes 34C of the first array of loop electrodes 30 is configured to contact or enter into a second cornu 106 of the body cavity 100, and another one of the loop electrodes 34A of the first array of loop electrodes 30 is configured to directly contact the fundus or uterine wall or tissue 108 surrounding or defining the body cavity 100.

The loop electrodes 46B, 46C, and 46A of the second array of loop electrodes 32 (46A is not shown in FIG. 4 because loop electrode 46A is projecting out of the page) are configured to directly contact the uterine wall or tissue 108 surrounding or defining the body cavity 100.

In FIGS. 5A-5D, for the sake of clarity, the loop electrodes 34A, 34B, 34C of the first array of loop electrodes 30 and the loop electrodes 46A, 46B, 46C of the second array of loop electrodes 32 are illustrated schematically inside of the body cavity 100 in the extended or expanded state.

The loop electrodes 34A, 34B, 34C, 46A, 46B, 46C are each in electrical communication with the power source 24. The loop electrodes 34A, 34B, 34C, 46A, 46B, 46C are configured to cooperate with each other and the power source 24 to deliver a therapy current to the body cavity 100 to medically effect or ablate the one or more portions of the body cavity 100, like the uterine wall or tissue 108 surrounding or defining the body cavity 100, the one or more cornu 106, 108, etc.

The therapy current may be a bipolar therapy current that is electrically communicated or passed between or amongst two or more loop electrodes 34A, 34B, 34C of the first array of loop electrodes 30; or between or amongst two or more loop electrodes 46A, 45B, 46C of the second array of loop electrodes 32; or a combination thereof. The therapy current may also be electrically communicated or passed between or amongst two or more loop electrodes 34A, 34B, 34C, 46A, 46B, 46C of the first and second array of loop electrodes 30, 32.

The therapy current may be passed or electrically communicated between or amongst two or more loop electrodes 34A, 34B, 34C, 46A, 46B, 46C, which results in the one or more features of the body cavity 100 that is/are in contact with the two or more loop electrodes 34A, 34B, 34C, 46A, 46B, 46C to heat up to an ablative temperature to medically or therapeutically effect the tissue, anatomy, body cavity, and/or uterus.

Figure 5A:
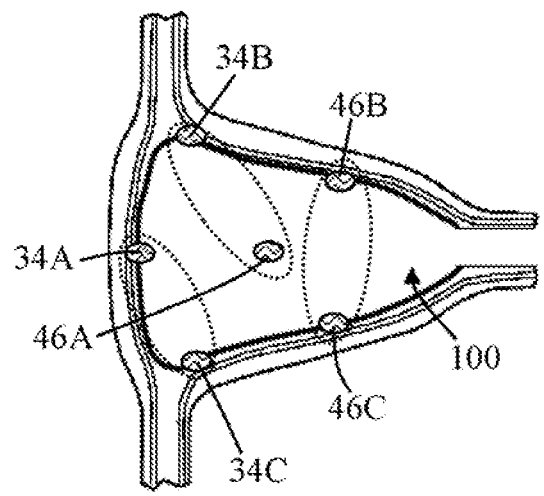
FIGS. 5A-5D are side views of a distal portion of the medical device of FIG. 1 inserted into a body cavity.

Referring to FIG. 5A, a therapy current may be passed between loop electrode 34B and loop electrode 46A; between loop electrode 46B and loop electrode 46C; and between loop electrode 34C and loop electrode 34A.

Figure 5B:
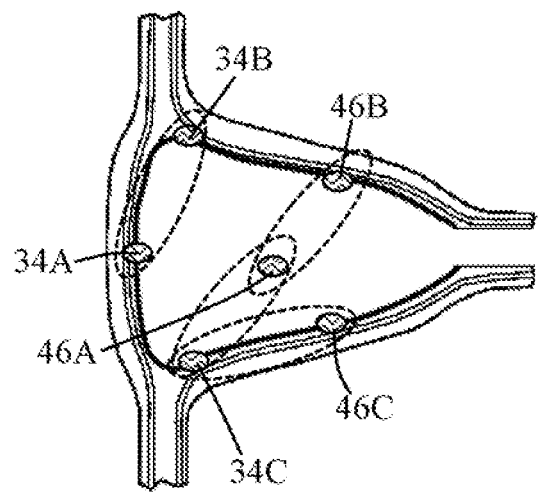

Referring to FIG. 5B, a therapy current may be passed between loop electrode 34B and loop electrode 34A; between loop electrode 46B and loop electrode 46A; between loop electrode 46C and loop electrode 34C; and between loop electrode 34C and loop electrode 46A.

Figure 5C:
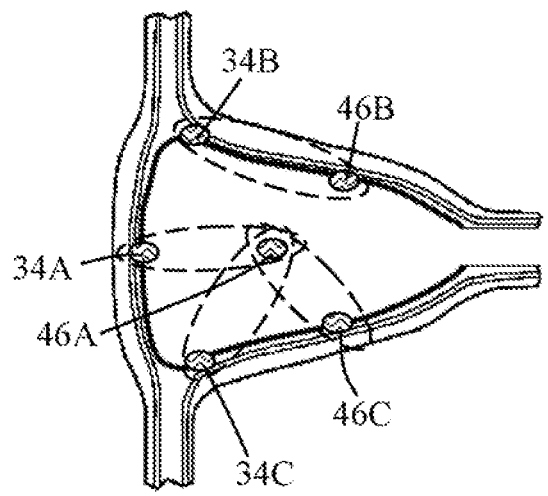

Referring to FIG. 5C, a therapy current may be passed between loop electrode 34B and loop electrode 46B; between loop electrode 34A and loop electrode 46A; between loop electrode 34C and loop electrode 46A; and between loop electrode 46C and loop electrode 46A.

Figure 5D:
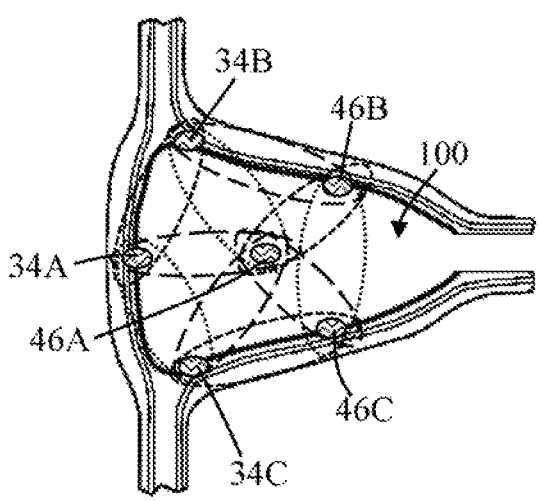

The passing of the therapy current between the loop electrodes 34A, 34B, 34C, 46A, 46B, 46C illustrated and described in FIGS. 5A-5C is summarized in FIG. 5D.

The passing of the therapy current between or amongst two or more of the loop electrodes 34A, 34B, 34C, 46A, 46B, 46C illustrated and described in FIGS. 5A-5D may occur at substantially the same time, one after another, at random, according to a pre-programed sequence or a combination thereof.

For example, the passing of the therapy current between electrodes in FIG. 5A, may be followed by the exchange in FIG. 5B, which may be followed by the Exchange in FIG. 5C, which may then be followed by the exchange in FIG. 5A, and so on to achieve a pattern illustrated in FIG. 5D and to achieve a global therapeutic effect on the body cavity 100 or globally ablate the body cavity 100.

Alternatively, the therapy current may be passed between or amongst the various loop electrodes at random, or not according to a preset or defined pattern. For example, the communication of therapy current in FIG. 5A may be followed by the exchange in FIG. 5C, which may be followed by the exchange in FIG. 5A, which may be followed by the exchange in FIG. 5B, which may be followed by the exchange in FIG. 5C, and so on, to achieve a global therapeutic effect on the body cavity 100 illustrated in FIG. 5D.

In either configuration (passing of the therapy current according to a pattern or randomly), the passing of the therapy current in each FIG. 5A-5C does not require a particular sequence or pattern amongst the loop electrodes. For example, referring to FIG. 5A, the therapy current may be passed between loop electrode 34B and loop electrode 46A before, during, or after the therapy current is passed between loop electrode 46B and loop electrode 46C, which may be before, during, or after the therapy current is passed between loop electrode 34C and loop electrode 34A. However, in some configurations, the therapy current may be exchanged according to a preset sequence or pattern. As an example, with continued reference to FIG. 5A, the therapy current may be passed between loop electrode 34B and loop electrode 46A, which is passed before the therapy current is passed between loop electrode 46B and loop electrode 46C, which is passed before the therapy current is passed between loop electrode 34C and loop electrode 34A.

Figure 6:
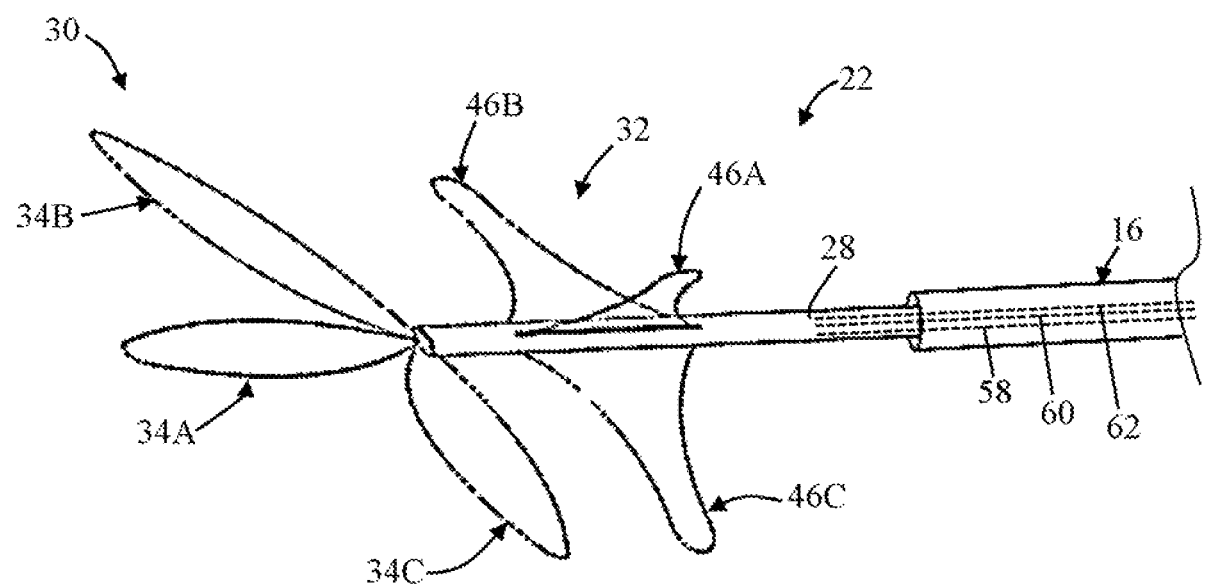
FIG. 6 is a perspective view of a distal portion of the medical device of FIG. 1, with the first and second arrays of loop electrodes in an expanded or extended state.

FIG. 6 illustrates a distal portion of the medical device 10. The effector 22 is substantially similar to the effector 22 illustrated in FIG. 2 and described herein; thus, the description of similar or like elements will be omitted.

In the effector 22 of FIG. 6, two or more of the loop electrodes 34A, 34B, 34C, 46A, 46B, 46C may be formed from a common wire or conductor. More specifically, one or more loop electrodes 34A, 34B, 34C from the first or distal array of loop electrodes 30 and one or more loop electrodes 46A, 46B, 46C from the second or proximal array of loop electrodes 32 may be formed from a common conductor or wire.

For example, a wire or conductor 58 may extend from the power source 24 (FIG. 1) to the effector 22 to form loop electrode 46C, then continue to form loop electrode 34C, and then extend back to the power source 24 to complete an electrical circuit. The wire or conductor 58 may be passed through the introducer 16 and/or carrier 28 between the power source 24 and each of the loops 46C, 34C. This common wire or conductor 58 is connected to the power source 24 such that during a medical procedure, the loops 46C, 34C have the same or common electrical potential.

Similarly, another wire or conductor 60 may extend from the power source 24 (FIG. 1) to the effector 22 to form loop electrode 46A, then continue to form loop electrode 34A, and then extend back to the power source 24 to complete an electrical circuit. The wire or conductor 60 may be passed through the introducer 16 and/or carrier 28 between the power source 24 and each of the loops 46A, 34A. This common wire or conductor 60 is connected to the power source 24 such that during a medical procedure, the loops 46A, 34A have the same or common electrical potential.

A third wire or conductor 62 may extend from the power source 24 (FIG. 1) to the effector 22 to form loop electrode 46B, then continue to form loop electrode 34B, and then extend back to the power source 24 to complete an electrical circuit. The wire or conductor 62 may be passed through the introducer 16 and/or carrier 28 between the power source 24 and each of the loops 46B, 34B. This common wire or conductor 62 is connected to the power source 24 such that during a medical procedure, the loops 46B, 34B have the same or common electrical potential.

Of course in some configurations, a common wire or conductor may form two other loops like: 46C and 34B, for example; 46A and 34C, for example; 46B and 34A; or any other combination thereof.

In another configuration, a common wire or conductor may form more than one loop in the second or proximal array of loop electrodes 32 and/or more than one loop in the first or distal array of loop electrodes 30. For example, a common wire or conductor may form loop 34C and 34A, and another wire may form loop 34B. For example, a common wire or conductor may form all loops 34C, 34B, and 34A so that during a medical procedure, loops 34C, 34B, and 34A have a common electrical potential. For example, a common wire or conductor may form loop 46C and 46A, and another wire may form loop 46B. For example, a common wire or conductor may form all loops 46C, 46B, and 46A so that during a medical procedure, loops 46C, 46B, and 46A have a common electrical potential.

In FIGS. 7A-7D, the effector 22 of FIG. 6 is illustrated inside of the body cavity 100 in the extended or expanded state. For the sake of clarity, the loop electrodes 34A, 34B, 34C of the first array of loop electrodes 30 and the loop electrodes 46A, 46B, 46C of the second array of loop electrodes 32 are illustrated schematically inside of the body cavity 100 in the extended or expanded state.

As was discussed above at FIG. 6, the first group of loop electrodes 46C, 34C are formed from a common conductor or wire 58; the second group of loop electrodes 46A and 34A are formed from a common conductor or wire 60; and the third group of loop electrodes 46B, 34B are formed from a common conductor or wire 62.

Each conductor or wire 58, 60, 62 is in electrical communication with the power source 24. This means that each of the groups of loop electrodes 46C, 34C; 46A, 34A; and 46B, 34B has an electrical potential depending on the pole of the power source 24 that the conductor or wire 58, 60, 62 is connected to and/or depending the potential being transmitted from the power source 24 to the corresponding conductor or wire 58, 60, 62.

For example, the conductor or wire 58 used to form loops 46C, 34C may be configured to provide a positive potential, the conductor or wire 60 used to form loops 46A, 34A may be configured to provide a negative potential, and the conductor or wire 62 used to form loops 46B, 34B may be configured to provide a negative potential, or any combination thereof.

The power source 24 may also be configured to switch the electrical potential so that during one therapeutic application, for example, one group of loops 46C, 34C may be configured to provide a positive potential, loops 46C, 34A may be configured to provide a negative potential, and loops 46B, 34B may be configured to provide a negative potential, and then during another therapeutic application, for example, loops 46C, 34C may be configured to provide a negative potential, loops 46A, 34A may be configured to provide a positive potential, and loops 46B, 34B may be configured to provide a positive potential.

The therapy current may be a bipolar therapy current that is electrically communicated or passed between or amongst the groups of loop electrodes 46C, 34C; 46A, 34A; and 46B, 34B, which results in the one or more features of the body cavity 100 that is/are in contact with groups of loop electrodes 46C, 34C; 46A, 34A; and 46B, 34B to heat up to an ablative temperature to therapeutically effect the body cavity 100.

Figure 7A:
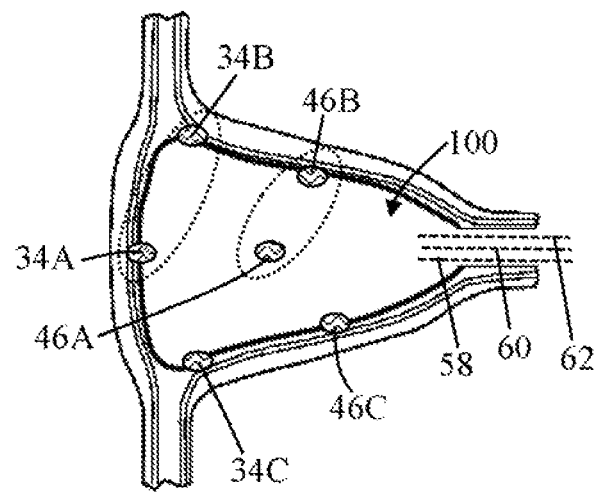
FIGS. 7A-7D are side views of a distal portion of the medical device of FIG. 6 inserted into a body cavity.

For example, referring to FIG. 7A, a therapy current may be passed between loop electrodes 34A and 34B and loop electrode 46A and 46B. A therapy current may also be passed between loop electrodes 34A and 46B and loop electrode 46A and 34B.

Figure 7B:
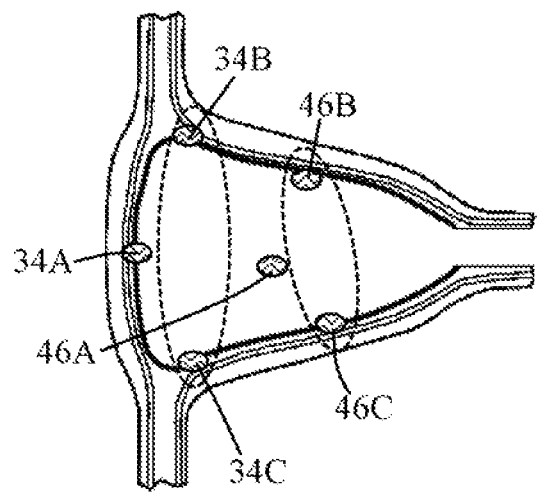
Figure 7C:
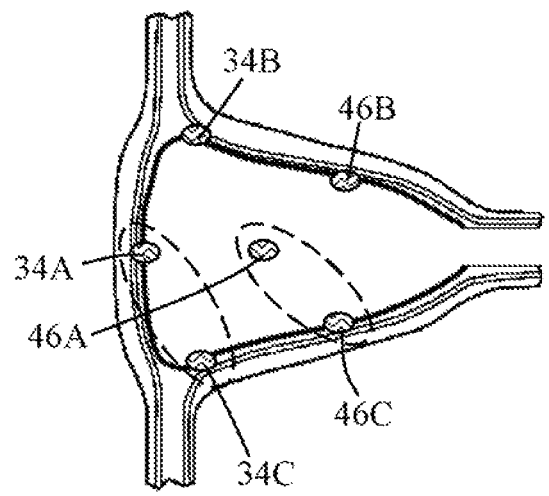

For example, referring to FIG. 7C, a therapy current may be passed between loop electrode 34B and loop electrode 34C and between loop electrode 46B and loop electrode 46C. A therapy current may be passed between loop electrode 34A and loop electrode 46C and between loop electrode 46A and loop electrode 34C.

For example, referring to FIG. 7C, a therapy current may be passed between loop electrode 34A and loop electrode 34C and between loop electrode 46A and loop electrode 46C. A therapy current may be passed between loop electrode 34A and loop electrode 46C and between loop electrode 46A and loop electrode 34C.

Figure 7D:
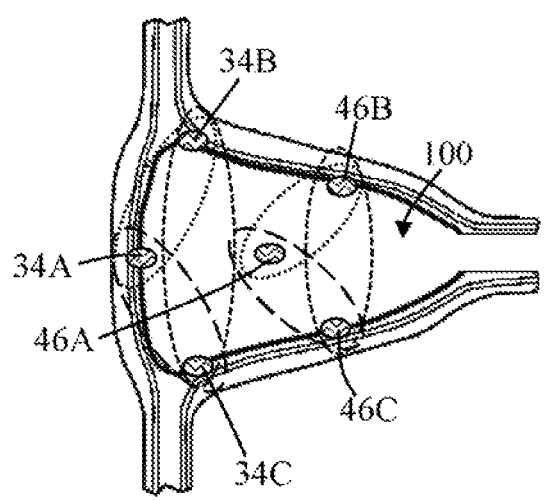

The passing of the therapy current between the loop electrodes 34A, 34B, 34C, 46A, 46B, 46C illustrated and described in FIGS. 7A-7C is summarized in FIG. 7D.

The passing of the therapy current between or amongst the groups of loop electrodes 34A, 34B; 46A, 46B; 34B, 34C; 46B, 46C; 34A, 34C and 46A, 46C illustrated and described in FIGS. 7A-7D may occur at substantially the same time, one after another, at random, according to a pre-programed sequence or a combination thereof.

For example, the passing of the therapy current between the electrodes in FIG. 7A, may be followed by the exchange in FIG. 7B, which may be followed by the exchange in FIG. 7C, which may then be followed by the exchange in FIG. 7A, and so on to achieve a pattern illustrated in FIG. 7D and to achieve a global therapeutic effect on the body cavity 100 or globally ablate the body cavity 100.

Alternatively, the therapy current may be passed between or amongst the various loop electrodes at random, or not according to a preset or defined pattern. For example, the communication of therapy current in FIG. 7A may be followed by the exchange in FIG. 7C, which may be followed by the exchange in FIG. 7A, which may be followed by the exchange in FIG. 7B, which may be followed by the exchange in FIG. 7C, and so on, to achieve a global therapeutic effect on the body cavity 100 illustrated in FIG. 7D.

The medical device 10 according to these teachings is configured to create, apply, and/or produce a global therapeutic effect on tissue or a body cavity. The global therapeutic effect is achieved with the device 10 according to these teachings without requiring a surface to surface contact with the body cavity as may be the case with some other devices that comprise a heated inflated surface or balloon that is configured to contact a surface of the body cavity. In such devices, for example, the balloon surface may not contact all areas of the body cavity due to size and shape differences amongst the different body cavities and amongst the size and shape differences amongst patients, which may result in certain areas of the anatomy receiving different amounts of therapy. To remedy such a short coming, a user may be required to manipulate, rotate, and/or sweep the device so that the heated balloon surface contacts all surfaces of the body cavity. However, as can be imagined, such movement of the device may cause user fatigue prolong a medical procedure, cause tissue perforation or damage, etc. Furthermore, such devices that include an inflated balloon require additional components, such as an inflator and deflator to inflate and deflate the balloon, which may result a more expensive and complicated device.

In contrast, by providing a medical device according to these teachings that includes loop electrodes that are configured to extend or expand from the medical device and conform to the anatomy of the body cavity, substantially equal pressure may be applied onto the anatomy of the body cavity. Then, by passing or sequencing a therapy current between two or more electrodes that are in contact with tissue of the body cavity, set of therapy regions can be painted inside of the body cavity that can overly produce the global therapeutic effect on or within the body cavity.

LISTING OF REFERENCE NUMERALS 10 medical device
12 hand piece
14 user controls
16 introducer
18 proximal end
20 distal end
22 effector
24 power source
26 electrical conductors
28 carrier
30 first array of loop electrodes
32 second array of loop electrodes
34 loop electrodes
36 distal-most end of the medical device 10 or carrier 28
38 base section
40 tip
42 legs
44 legs
46 loop electrodes
48 slits or openings
50 base
52 tip
54 leg
56 leg
58 conductor or wire
60 conductor or wire
62 conductor or wire
A axis
P plane
100 body cavity
102 opening
104 cornu
106 cornu
108 tissue defining the body cavity 100

The explanations and illustrations presented herein are intended to acquaint others skilled in the art with the invention, its principles, and its practical application. The above description is intended to be illustrative and not restrictive. Those skilled in the art may adapt and apply the invention in its numerous forms, as may be best suited to the requirements of a particular use.

Accordingly, the specific embodiments of the present invention as set forth are not intended as being exhaustive or limiting of the teachings. The scope of the teachings should, therefore, be determined not with reference to this description, but should instead be determined with reference to the appended claims, along with the full scope of equivalents to which such claims are entitled. The omission in the following claims of any aspect of subject matter that is disclosed herein is not a disclaimer of such subject matter, nor should it be regarded that the inventors did not consider such subject matter to be part of the disclosed inventive subject matter.

Plural elements or steps can be provided by a single integrated element or step. Alternatively, a single element or step might be divided into separate plural elements or steps.

The disclosure of "a" or "one" to describe an element or step is not intended to foreclose additional elements or steps.

While the terms first, second, third, etc., may be used herein to describe various elements, components, regions, layers and/or sections, these elements, components, regions, layers and/or sections should not be limited by these terms. These terms may be used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The disclosures of all articles and references, including patent applications and publications, are incorporated by reference for all purposes. Other combinations are also possible as will be gleaned from the following claims, which are also hereby incorporated by reference into this written description.

The invention claimed is:

1. A medical device comprising:
   an introducer extending along a longitudinal axis and including a proximal end, a distal end, and an internal lumen;
   a carrier extending along the longitudinal axis and at least partially disposed within the internal lumen of the introducer, the carrier movable in a proximal direction and in a distal direction relative to the introducer;
   a first array of loop electrodes disposed on the carrier; and
   a second array of loop electrodes disposed on the carrier;
   wherein the carrier is movable in the proximal and distal directions between a retracted position where the first and second arrays of loop electrodes are disposed within the internal lumen in a collapsed configuration and an extended position where the first and second arrays of loop electrodes extend distally beyond the distal end of the introducer in an expanded configuration;
   wherein the first array of loop electrodes protrudes from and extends distally beyond a distal end of the carrier in the expanded configuration;
   wherein the first array of loop electrodes extends radially outward from the longitudinal axis by a first distance in the expanded configuration;
   wherein the second array of loop electrodes extends radially outward from the longitudinal axis by a second distance in the expanded configuration, the second distance being less than the first distance; and
   wherein the first array of loop electrodes and the second array of loop electrodes are configured to deliver a therapy current to tissue defining the uterus.

2. The medical device according to claim 1, wherein when the carrier is in the extended position, the first array of loop electrodes extends from a distal-most end of the carrier and the second array of loop electrodes are circumferentially arranged around the longitudinal axis in a position proximal to the first array of loop electrodes and proximal to the distal-most end of the carrier.

3. The medical device according to claim 1, wherein the first array of loop electrodes comprises one or more loop electrodes that have a petal shape, and
   wherein one or more loop electrodes in the second array of loop electrodes have a triangular shape.

4. The medical device according to claim 3, wherein the first array of loop electrodes comprises three or fewer loop electrodes configured to expand from a distal-most end of the medical device.

5. The medical device according to claim 2 wherein two or more loop electrodes in the first array are located in a single plane.

6. The medical device according to claim 2, wherein the second array of loop electrodes comprises loop electrodes that are equally spaced around the longitudinal axis.

7. The medical device according to claim 2, wherein the therapy current is a bipolar therapy current that is communicated between the first array of loop electrodes and the second array of loop electrodes.

8. The medical device according to claim 2, wherein the therapy current is a bipolar therapy current that is communicated amongst two or more loop electrodes in the first array of loop electrodes and amongst two or more loop electrodes in the second array of loop electrodes.

9. The medical device according to claim 6, wherein one or more of the loop electrodes in the first array of loop electrodes have a petal shape, and one or more of the loop electrodes in the second array of loop electrodes have a triangular shape,
   wherein one of the loop electrodes of the first array of loop electrodes is configured to contact or enter a cornu of the uterus, and one of the loop electrodes of the second array of loop electrodes is configured to directly contact a uterine wall of the uterus.

10. The medical device according to claim 8, wherein the first array of loop electrodes comprises exactly three loop electrodes, and the second array of loop electrodes comprises exactly three loop electrodes.

11. A medical device comprising:
    an introducer extending along a longitudinal axis and including a proximal end, a distal end, and an internal lumen;
    a carrier extending along the longitudinal axis and at least partially disposed within the internal lumen of the introducer, the carrier movable in a proximal direction and in a distal direction relative to the introducer;
    a first array of loop electrodes disposed on the carrier, the first array of loop electrodes comprising two or more loop electrodes that are arranged in a single plane; and
    a second array of loop electrodes disposed on the carrier;
    wherein the first and second arrays of loop electrodes are configured to expand within a uterus and deliver a therapy current to the uterus when the carrier is moved from a retracted position where the first and second arrays of loop electrodes are disposed within the internal lumen in a collapsed configuration to an extended position where the first and second arrays of loop electrodes extend distally beyond the distal end of the introducer in an expanded configuration;
    wherein the first array of loop electrodes protrudes from and extends distally beyond a distal end of the carrier in the expanded configuration;
    wherein the first array of loop electrodes extends radially outward from the longitudinal axis by a first distance in the expanded configuration; and
    wherein the second array of loop electrodes extends radially outward from the longitudinal axis by a second distance in the expanded configuration, the second distance being less than the first distance.

12. The medical device according to claim 11, wherein the two or more loop electrodes of the first array have a petal shape.

13. The medical device according to claim 11, wherein one of the two or more loop electrodes of the first array is configured to contact or enter a cornu of the uterus.

14. The medical device according to claim 13, wherein the two or more loop electrodes of the first array comprise exactly three loop electrodes.

15. The medical device according to claim 11, wherein the therapy current is a bipolar therapy current that is communicated between the two or more loop electrodes of the first array.

16. A medical device comprising:
an introducer extending along a longitudinal axis and including a proximal end, a distal end, and an internal lumen;
a carrier extending along the longitudinal axis and at least partially disposed within the internal lumen of the introducer, the carrier movable in a proximal direction and in a distal direction relative to the introducer;
a first array of loop electrodes disposed on the carrier, the first array of loop electrodes comprising three or more loop electrodes that are circumferentially arranged about the longitudinal axis; and
a second array of loop electrodes disposed on the carrier, the second array of loop electrodes comprising two or more loop electrodes that are circumferentially arranged about the longitudinal axis;
wherein the first and second arrays of loop electrodes are configured to expand within a uterus and deliver a therapy current to tissue defining the uterus when the carrier is moved from a retracted position where the first and second arrays of loop electrodes are disposed within the internal lumen in a collapsed configuration to an extended position where the first and second arrays of loop electrodes extend distally beyond the distal end of the introducer in an expanded configuration;
wherein the first array of loop electrodes protrudes from and extends distally beyond a distal end of the carrier in the expanded configuration;
wherein the first array of loop electrodes extends radially outward from the longitudinal axis by a first distance in the expanded configuration; and
wherein the second array of loop electrodes extends radially outward from the longitudinal axis by a second distance in the expanded configuration, the second distance being less than the first distance.

17. A medical device comprising:
an introducer extending along a longitudinal axis and including a proximal end, a distal end, and an internal lumen;
a carrier extending along the longitudinal axis and at least partially disposed within the internal lumen of the introducer, the carrier movable in a proximal direction and in a distal direction relative to the introducer;
a distal array of loop electrodes disposed on the carrier, the distal array of loop electrodes comprising a first loop electrode and a second loop electrode;
a proximal array of loop electrodes disposed on the carrier, the proximal array of loop electrodes comprising a first loop electrode and a second loop electrode;
a first conductor wire forming the first loop electrode of the distal array of loop electrodes and the first loop electrode of the proximal array of loop electrodes; and
a second conductor wire forming the second loop electrode of the distal array of loop electrodes and the second loop electrode of the proximal array of loop electrodes;
wherein the distal array of loop electrodes and the proximal array of loop electrodes are configured to expand within a uterus and deliver a therapy current to tissue defining the uterus when the carrier is moved from a retracted position where the distal and proximal arrays of loop electrodes are disposed within the internal lumen in a collapsed configuration to an extended position where the distal and proximal arrays of loop electrodes extend distally beyond the distal end of the introducer in an expanded configuration;
wherein the distal array of loop electrodes protrudes from and extends distally beyond a distal end of the carrier in the expanded configuration;
wherein the distal array of loop electrodes extends radially outward from the longitudinal axis by a first distance in the expanded configuration; and
wherein the proximal array of loop electrodes extends radially outward from the longitudinal axis by a second distance in the expanded configuration, the second distance being less than the first distance.

18. The medical device according to claim 17, wherein the first loop electrode of the distal array of loop electrodes and the second loop electrode of the distal array of loop electrodes are both located in a single plane.

19. The medical device according to claim 17, wherein the first loop electrode of the proximal array of loop electrodes and the second loop electrode of the proximal array of loop electrodes are circumferentially arranged around the longitudinal axis in a position proximal to the distal array of loop electrodes.

20. The medical device according to claim 17, wherein the first conductor wire is connected to a first pole of a power source and the second conductor wire is connected to a second pole of the power source so that the first conductor wire has a different electrical potential than the second conductor wire.

21. The medical device according to claim 1, wherein in the expanded configuration, the first and second arrays of loop electrodes are sized and oriented such that they generally conform with a shape of the uterus, and at least one loop electrode of the first array is arranged to treat tissue distal to the carrier.

22. The medical device according to claim 1, wherein the first array of loop electrodes is disposed on a distal area of the carrier, wherein the second array of loop electrodes is disposed on a proximal area of the carrier, and wherein the distal area and the proximal area of the carrier project outwardly from the introducer in the extended position.

* * * * *